United States Patent [19]
Marks et al.

[11] Patent Number: 5,470,545
[45] Date of Patent: Nov. 28, 1995

[54] CORRIN MEDIATED DEGRADATION OF ORGANIC NITROGEN COMPOUNDS

[75] Inventors: Trevor S. Marks, Salisbury; Andrew Maule, Amesbury, both of Great Britain

[73] Assignee: The Public Health Laboratory Service Board in Her Britannic Majesty's Government of the United Kingdom of Great Britain and Northern Ireland, London, England

[21] Appl. No.: 773,938

[22] PCT Filed: May 9, 1990

[86] PCT No.: PCT/GB90/00715

§ 371 Date: Nov. 5, 1991

§ 102(e) Date: Nov. 5, 1991

[87] PCT Pub. No.: WO90/13336

PCT Pub. Date: Nov. 15, 1990

[30] Foreign Application Priority Data

May 10, 1989 [GB] United Kingdom ............... 8910760

[51] Int. Cl.[6] .................................................. A61L 2/20
[52] U.S. Cl. ...................... 422/292; 210/757; 210/758; 422/28; 422/32
[58] Field of Search ..................... 422/28, 32, 292; 588/205, 206; 210/757, 758, 762, 763

[56] References Cited

U.S. PATENT DOCUMENTS

| 3,252,892 | 5/1966 | Gleim. | |
|---|---|---|---|
| 4,128,621 | 12/1978 | Homeier. | |
| 4,256,670 | 3/1981 | Homeier. | |
| 4,372,893 | 2/1983 | Eckert | 358/302 |
| 5,004,551 | 4/1991 | Sublette | 210/763 |
| 5,032,291 | 7/1991 | Sublette | 210/757 |
| 5,120,453 | 6/1992 | Frame et al. | 210/759 |

FOREIGN PATENT DOCUMENTS

3012674 10/1982 Germany.

OTHER PUBLICATIONS

Mansuy et al., "Biochem Biophys. Res. Comm.", vol. 104, No. 4, Feb. 26, 1982 pp. 1651–1657.

*Primary Examiner*—Timothy M. McMahon
*Attorney, Agent, or Firm*—Nixon & Vanderhye

[57] ABSTRACT

A method of degrading an organic nitrogen compound to its reduction products, in which the compound is caused to react with a reducing agent in the presence of a complex of a corrin containing a metal-centered ring system. Preferred complexes are cobalt-centered hydrolysis products of Vitamin B12, such as cobyrinic acid, and in one embodiment these complexes are immobilised on a substrate. Using the method environmental pollutants such as nitrobenzenes may be rapidly reduced.

15 Claims, 2 Drawing Sheets

Fig.1.

Dinoseb

Trifluralin

Parathion

CORRIN MEDIATED DEGRADATION OF ORGANIC NITROGEN COMPOUNDS

This invention relates to methods for the degradation of organic nitrogen-containing compounds, particularly nitro-compounds, using corrins to catalyse or accelerate the degradation.

Organic nitrogen compounds present an environmental pollution problem. They may enter soil and aquatic environments by many routes and may threaten the drinking water supply. Such compounds include organic nitro- and nitroso-compounds, nitriles, thiocyanates and isothiocyantes among others. Nitro- and nitroso-compounds are for example believed to be carcinogenic.

Figure 1:
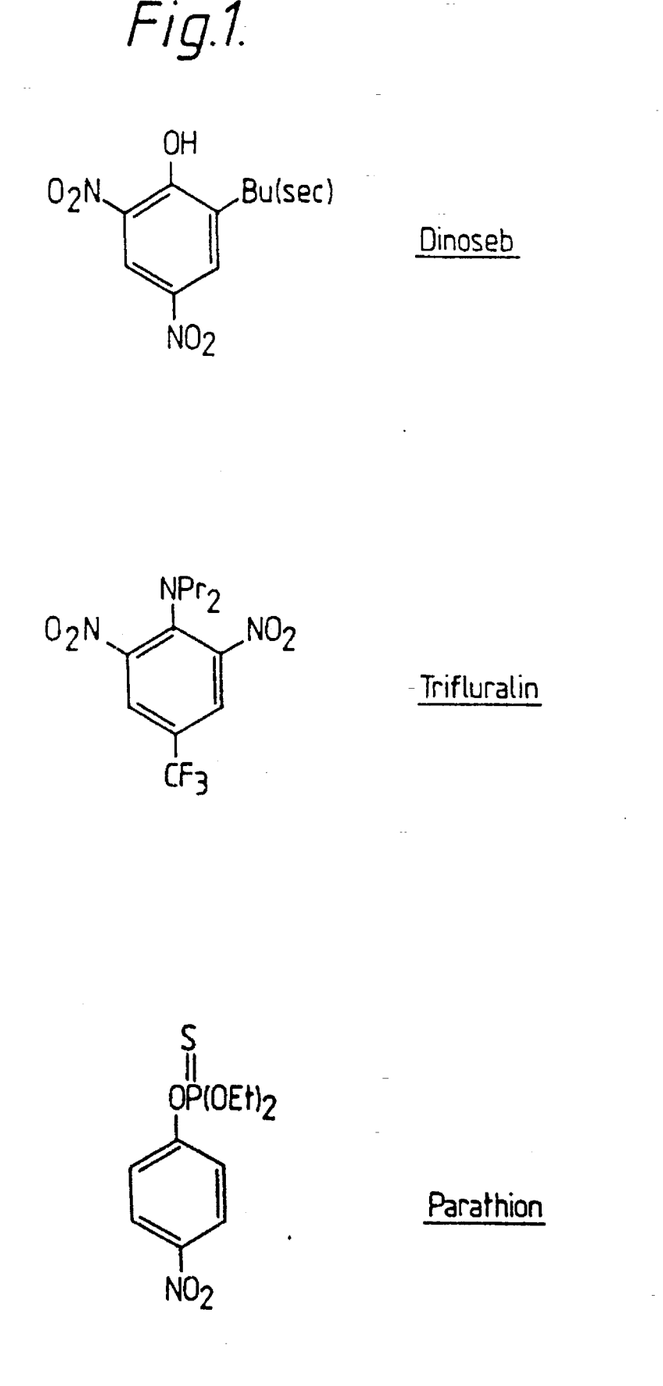

Such compounds are used or generated in large quantities in some chemical industries, eg explosive and dye making, and can hence be contained in industrial effluent. Some organic nitro compounds are used as herbicides, eg "Dinoseb" and "Trifluralin", or insecticides eg "Parathion" (Trade Marks), whose structures are shown in FIG. 1. Such compounds are hence introduced directly into the environment, or may enter the environment indirectly through grazing animals which have ingested the compounds. Many such herbicides suffer from the problem of "persistence", ie they are not easily broken down by nature into less harmful compounds.

Currently used methods for the disposal or destruction of such compounds, eg incineration and landfill or offshore dumpings are not ideal and can lead to further pollution. There is therefore a need for improved methods of disposal of the compounds, especially via their degradation into less harmful compounds or into compounds which are more readily broken down by nature, eg through oxidation, photodecomposition, hydrolysis or biologically.

It is known (eg Mansuy and Fontecove (1982), Miwa and Walsh (1988), Lindeke and Paulsen-Sörman (1988)) that certain iron-centred porphyrins are capable of catalysing oxidation-reduction reactions of organic nitrogen compounds such as amines, nitro and nitroso compounds, oximes and cyano compounds. It is also known (eg Stotter (1977)) that such porphyrins can catalyse reductive dehalogenation of organic halides.

Porphyrins are large cyclic amines containing the ring system (1):

in which two of the four central nitrogen atoms may be bonded to hydrogen atoms, or else all four may be co-ordinated to a central metal atom or ion such as iron in the references mentioned.

The porphyrin ring in these complexes normally carries a number of peripheral substituents, and it is know that relatively small variation of these peripheral substituents can have a drastic effect on the ability of the porphyrin-metal complexes to dehalogenate organic halides (see for example discussion in GB 88 10944). For example iron III haematoporphyrin dehalogenates 1,2,3,4,5,6-hexachlorocyclohexane very effectively whilst iron III copropophyrin has no catalytic effect, there being relatively little difference between the substitution patterns. Little can therefore be said for certain about the effect of changes in the peripheral structure of such complexes on their catalytic ability.

Corrins are large cyclic amines having a 19-membered peripheral ring system which can exist in a number of isomeric forms in which the position of double and single bonds in the peripheral ring can vary, as will be seen in the discussion of structures 2A–2H below. The general abbreviation (2):

is used herein for all isomeric forms of the corrin ring system.

In a similar fashion to porphyrin systems, one or more of the central nitrogen atoms in a corrin may be bonded to one or more hydrogen atoms, or all 4 may be co-ordinated to a central metal atom, which may itself be additionally complexed with one or more other ligands, for example to form the metal-co-ordinated centre:

where M is a metal atom or ion, and where $L_1$ and $L_2$ if present represent the same or different ligands.

Corrins containing metal centres are known, for example the cobalt centred corrins found in the vitamin B12 series of compounds, eg vitamin B12 itself, ie cyanocobalamin, also known simply as cobalamin (2A):

(2A)

Closely related to cyanocobalamin (2A) is dicyanocobalamin, which has a structure analogous to cyanocobalamin but in which two CN ligands are coordinated to the central cobalt ion and the ribazole residue does not chelate with the cobalt.

Other known cobalt centred corrins include hydroxycobalamin, adenosylcobalamin and cobaloximes.

Other known cobalt-centred corrins are those described by Bonnett et al (1971) ie Neovitamin B12, a stereoisomer of (2A) in which the H and $CH_2CH_2CONH_2$ substituents at ring position 13 are transposed, and the compounds (2Bi-vi) of structure:

i    Cobinamide $R^1 = NH_2$, $R^2 = H$, $R^3 =$

| | |
|---|---|
| | $CH_2$ $CH_2$ $CONH_2$, $R^4 = NHCH_2CH(OH)Me$. |
| ii | Neocobinamide $R^1 = NH_2$, $R^2 = CH_2$ $CH_2$ $CONH_2$, $R^3 =$ H, $R^4 = NH$ $CH_2$ $CH(OH)Me$. |
| iii | Cobyric Acid $R^1 = NH_2$, $R^2 = H$, $R^3 =$ $CH_2$ $CH_2$ $CONH_2$, $R^4 = OH$. |
| iv | Neocobyric Acid $R^1 = NH_2$, $R^2 =$ $CH_2$ $CH_2$ $CONH_2$, $R^3 = H$, $R^4 = OH$. |
| v | Heptamethyl Cobyrinate $R^1 = R^4 = OMe$, $R^2 =$ H, $R^3 = CH_2$ $CH_2$ $CO_2$ Me. |
| vi | Heptamethyl Neocobyrinate $R^1 = R^4 = OMe$, $R^2 =$ $CH_2$ $CH_2$ $CO_2$ Me, $R^3 = H$. |

Cobalt centred corrins of formula (2C and D) are described by Gossauer et al (1977):

| 2C  | R       | L         | 2D  | R                                    |
|-----|---------|-----------|-----|--------------------------------------|
| i   | H       | CN        | i   | H                                    |
| ii  | H       | SCN or NCS| ii  | Br                                   |
| iii | Br      | CN        | iii | I                                    |
| iv  | I       | CN        | iiv | NO$_2$                               |
| v   | NO$_2$  | CN        | v   | NH$_2$                               |
| vi  | NH$_2$  | CN        | vi  | NH$_3^+$ CF$_3$COO$^-$               |
| vii | NHCOCH$_3$ | CN     | vii | NHCOCH$_3$                           |

Bormann et al (1967) describes cobalt and nickel centred corrins of formulae (2E), (2F) and (2G):

| 2E | Fl | R$^1$ |
|----|----|----|
| i  | H  | H  |
| ii | CN | H  |

| 2f | Fl | R$^1$ |
|----|----|----|
| i  | H  | H  |
| ii | CN | H  |

Bieganowski and Friedrich (1980) also describe Fe (III) centred analogues of cyanocobalamin (2A) and cobyric acid (2Biii).

Holze and Gossauer (1986) describe various degradation products of cyanocobalamin (2A) including (2H) in which the ribazole residue has been removed:

(2H)

Some investigations of dehalogenation of organo-halogen compounds by corrins have been carried out, as briefly reviewed below.

Bieniek et al (1970) describes the dehalogenation of lindane by cyanocobalamin. Both Bieniek (op cit) and Stotter (1976) refer to the dehalogenation of dieldrin (3) by cyanocobalamin. Neither of these references gives any kinetic data for the reactions of cyanocobalamin with these organohalides. Stotter (1976) and Jagnow et al (1977) refer to in vivo reactions between cyanocobalamin and a number of organohalides including chloromethanes, chloral hydrate and lindane. The degradation of DDT in cyanocobalamin-rich sewage sludge has been observed (Stotter op cit). Little work has been carried out however to identify the corrins which are most effective in the dehalogenation of organohalides, or optimum conditions under which dehalogenation may take place, and none appears to have been carried out on the ability of corrins to degrade organic nitrogen compounds.

By virtue of their being naturally occurring and hence potentially cheap, corrins are attractive compounds for use in the degradation of pollutants.

It is an object of the invention to provide a novel method using novel or known metal-corrin complexes to degrade organic nitrogen compounds.

According to this invention, a method of degrading an organic nitrogen compound includes the step of causing the compound to react with a reducing agent in the presence of a complex of a corrin containing a metal centred ring system.

The method of this invention is suitable for degradation of a wide range of aliphatic and aromatic nitrogen compounds, the degradation leading to less harmful compounds or compounds which can be more easily broken down in the environment by natural forces.

The method is particularly suitable for the degradation of aliphatic or aromatic nitro- or nitroso-compounds, ie containing one or more $-NO_2$, $-ONO_2$ or $-NO$ groups. In aromatic compounds these may be attached directly to an aromatic, eg phenyl, ring or located on a side chain. In such cases degradation by the method of the invention results in reduction to the corresponding amine. Examples of the types of aromatic nitro- and nitroso-compounds which may be degraded using the method of the invention include nitrobenzenes, dinitrobenzenes, nitrosobenzenes, and their analogues with additional alkyl, halogen or carboxylate substituents on the ring(s) and/or side chains. The method is also suitable for the degradation of organic nitro-compounds used as herbicides or insecticides, eg Dinoseb, Trifluralin and Parathion.

The method is also suitable for the degradation of aliphatic and aromatic thiocyanates (SCN) isothiocyantes (NCS) and nitriles (CN). It may indeed be suitable for degradation of other nitrogen compounds such as aliphatic or aromatic N-oxides, (N→O), oximes (=N—OH), azoxy compounds $(-N=N-)$, nitroparaffins, nitro-olefins, halogenonitroparaffins, nitronitroso compounds ($-C(NO)(NO_2)$), nitrolic acids ($-C(NO_2)=NOH$), nitroso-amines ($-N=NO$), nitroamines ($-NHNO_2$) and nitrosoalkylhydrazines ($-N(NO)NH_2$) etc, which are capable of chemical reduction to an amine or otherwise.

In the method of the invention the use of complexes of corrins having a general formula (2I):

(2I)

using the abbreviated general formula of the corrin ring, M being the metal atom or ion, A and B being the same or different coordinating ligands, and a and b each being 0 or 1, is preferred.

A preferred isomeric form for the corrin ring in 2I is that found in structures 2A and 2B. The corrin ring in 2I preferably has substituents on the ring which enhance the solubility of the complex in water or enhance its ability to be bound to a solid substrate (see later). Preferably there are up to 8 amide, hydroxyl or especially carboxylic acid terminated substituents in one or more of the 2, 3, 7, 8, 12, 13, 17 or 18 positions on the ring. Carboxylic acid and amide terminated substituents preferably have formulae $(CH_2)_nCOX$ where n is 0–3 and X is OH or $NR_1R_2$ where $R_1$ and $R_2$ are independently hydrogen. $C_{1-10}$ alkyl or $C_{1-10}$ hydroxy-substituted alkyl ie $(CH_2)_mCH(OH)C_pH_{2p+1}$ where m and p are independently 1–5. Hydroxyl terminated substituents include OH groups and $(CH_2)_nOH$ groups where n is 1–5.

Other substitution positions on the 2I ring if occupied by other than hydrogen are preferably occupied by substituents which do not interfere by sterically hindering the approach of the molecule to be degraded to the metal M, or else by causing a deleterious electron shift in the complex. Suitable substituents on these other positions include small (eg $C_{1-8}$) alkyl groups especially methyl, amino, cyano or ester groups, or monocyclic substituents such as in 2C. The method may also work but less satisfactorily when these other positions are occupied by larger organic residues such as the ribazole group present in dicyanocobalamin, but these may cause some interference.

The corrin ring system in complexes 2I may conveniently be, or be derived from, known corrin ring systems such as those in 2A–2H above. For example ester, amide and cyano substituents in 2A–2H may be hydrolysed to form carboxylic acid groups, which may then be converted to amide groups if desired by known methods. Additionally or alternately substituents such as the ribazole side chain of cyanocobalamin may be removed eg by hydrolysis of the phosphate ester link to yield cobinamide.

Preferred metals M in these corrin complexes are those of Group 2, 5, 6, 7, 8, 9, 10, 11 or 12 of the periodic table, but especially cobalt, nickel, molybdenum, iron and magnesium, particularly cobalt. In many cases corrin complexes of formula 2I in which M is other than cobalt may be prepared from known cobalt-corrin complex precursors such as those described above by reaction of a solution of the cobalt corrin complex with a chelating ligand which has a stronger affinity for cobalt than the corrin residue, such as EDTA, preferably to form an insoluble cobalt-chelating ligand complex which may easily be separated. This leaves a vacant co-ordination site in the centre of the corrin ring into which a metal ion M may be inserted by incubating the corrin with a solution of the metal ion.

Suitable conditions are reaction of the precursor with an equimolar amount of the chelating ligand in aqueous solution.

Preferred ligands A and B are inorganic ligands such as $ClO_4^-$, $SCN^-$, $SO_3^-$, $S_2O_3^{2-}$, $H_2O$ and in particular $CN^-$, $Cl^-$ or $OH^-$. As many corrin complexes are known with a $Co(CN)_2$ centre it is convenient to prepare cobalt corrin complexes in which A and B are other than CN starting from a $Co(CN)_2$ centred complex precursor by incubation of the precursor with an equimolar amount of the ligand in aqueous solution.

In formula 2I, (a+b) is preferably 2 if M is cobalt II or III, and 0 if M is Ni II.

Preferred complexes of formula 2I are the cobalt-centred complexes which are formed when cobalamin (2A) or Neovitamin B12 is hydrolysed, eg by heating with an aqueous alkali (eg NaOH) or acid (eg HCl).

Particularly preferred corrin-cobalt complexes of formula 2I are those of formula 2J:

in which $R^1$ is selected from $NH_2$ and OH, $R^2$ is selected from H, $CH_2CH_2COOH$ and $CH_2CH_2CONH_2$, $R^3$ is selected from H, $CH_2CH_2COOH$ and $CH_2CH_2CONH_2$, and $R^4$ is selected from $NHCH_2CH(OH)CH_3$, OH and $NH_2$.

Particularly preferred cobalt-corrin complexes of formula 2J are:

Cyanocobalamin and cyanocobalamin- $SCN^-$ or $S_2O_3^{2-}$ complexes, ie analogues of dicyanocobalamin having A=CN and B=SCN or $S_2O_3^{2-}$;

Cobinamide (2Bi), Neocobinamide (2Bii), Cobyric acid (2Biii), Neocobyric acid (2Biv), Cobyrinic acid (ie 2Bv having $R^1=R^4=OH$, $R^2=H$ $R^3=CH_2CH_2COOH$) and Neocobyrinic acid (ie (2Bvi having $R^1=R^4=OH$, $R^2=CH_2CH_2COOH$ $R^3=H$), is having A=B=CN and a and b being 1;

and analogues of Cobinamide, Neocobinamide, Cobyric acid, Neocobyric acid, Cobyrinic acid and Neocobyrinic acid in which the $Co(CN)_2$ centre is replaced by a CoAB centre in which A and B are selected from inorganic ligands other than $CN^-$, especially $Cl^-$ and $OH^-$.

The method of this invention is found to work over a range of temperatures, and the rate of degradation generally increases with increasing temperature. Conveniently ambient temperature (ca 20° C.) may be used, and an upper optimum practical limit appears to be (ca 80° C. In some cases illumination of the medium may be beneficial.

Because the metal-centred corrin complexes which are used in the method of the invention may in some cases have one or more functional substituents such as amine, amide, hydroxy, azo and acid groups and may in some cases have a complex stereochemistry, they may exist in a number of ionised or protonated forms depending upon the pH etc of the medium in which they are contained, and may also exist in a number of complexed forms or in an ionised form combined with a counter-ion eg $Cl^-$. The method of the invention includes all such forms of the complex, and all stereoisomeric forms thereof.

It is essential that the medium in which the reaction of the method takes place contains a reducing agent. These may be inorganic reducing agents such as borohydride, dithionite, sulphite, phosphite, hypo phosphite, sulphide etc. Organic reducing agents such as dithioerythreitol, dithiothreitol, mercaptosugars etc may also be used. Many such chemical reducing agents may be used and will be well known to those skilled in the art. Additionally or alternatively microorganisms which create a reducing environment or are capable of carrying out reduction may also be employed as a reducing agent, and included among these are known anaerobic microorganisms such as those which are found in soil.

The method of the invention is found to work over a wide range of concentrations of the complex, the organic nitrogen compound and the reducing agent. For quantitative degradation of the organic nitrogen compound it is important that the medium contains at least one molar equivalent of the reducing agent per mole of the nitrogen compound. Generally the complex is not used up in the method, but appears to function essentially as a catalyst assisting transfer of electrons from the reducing agent to the nitrogen compound. The ratio of complex to nitrogen compound therefore does not appear to be critical.

In many cases the kinetics of the reaction between the complex and the nitrogen compound shows first order kinetics, and hence the rate at which degradation occurs depends upon the relative concentrations of the complex and the nitrogen compound. These may be varied between wide limits and will depend upon the environment or medium in which the reaction occurs. For example the method may be used at concentrations of the nitrogen compound down to ppm level as encountered in many pollution situations, and experiments have shown the method to be effective at $1 \times 10^{-5}$M concentrations of the nitrogen compound.

The presence of other chemicals in the medium does not in many cases interfere with the method of the invention, but excess cyanide ion may be detrimental. This cyanide may be removed using known methods. A pH of about 9 appears to be optimum.

In an industrial environment, the method of the invention may for example be applied by simply mixing an appropriate quantity of the metal-corrin complex with an industrial waste solution which contains the undesirable nitrogen compound, ensuring that the solution is reducing, adjusting the pH and leaving the mixture to stand for a suitable length of time, during which the quantity of the nitrogen compound may be monitored. Other methods of treating such industrial wastes, or polluted rivers, lakes or ground etc will be apparent to those skilled in the field.

In a preferred way of performing the degradation method of the invention, the complex is immobilised on an insoluble substrate and a solution containing the organic nitrogen compound is brought into contact with the immobilised complex. To ensure that a reducing agent is present the solution may contain a reducing agent or the substrate may have a reducing agent bonded or absorbed onto it.

This way of performing the method offers the advantage that the method may be made continuous or semi continuous, ie a solution to be degraded (eg an industrial or agricultural effluent) may be passed through a bed containing a complex immobilised on a substrate, and the method need only be discontinued for regeneration of the bed, eg by passage of a reducing agent through the bed. The flow rate to achieve a suitable residence time for the nitrogen compound to be degraded depends inter alia on the nature of the compound to be degraded, concentration, temperature etc, but relatively simple experimentation can determine these parameters.

The substrate may be any insoluble material, preferably otherwise inert to the solution, onto which the complex can be immobilised. To ensure that the complex is firmly immobilised onto the substrate it is preferred that the complex is chemically bound to the substrate by means of interaction between functional group substituents on the corrin ring and appropriate functional group substituents on the substrate. As a consequence of the fact that the preferred corrin complexes (eg of formula 2J) have carboxylate (COOH) and amide ($CONH_2$) functional substituents on their rings respectively, preferred substrates are materials which have functional groups which are capable of combining with these on their surface. For example amine ($NH_2$) and amide groups on the substrate may react with carboxylate groups on the complex, and carboxylate groups on the substrate may react with amine or amide groups on the complex, to form chemical bonds.

Many suitable substrates having such functional groups are known in particular the substrates commonly used for affinity chromatography. For example derivatised polysaccharides such as celluloses, agarose, dextrose and dextran, polyacrylamides and copolymers of these materials such as polyacrylamide-agarose gells, which may be either cross linked or non-cross linked. Alternatively derivativised inorganic oxides such as silica, alumina, titania or zirconia, or glass beads may be used. Polymeric materials such as derivatised polystyrene or ion exchange resins can also be used.

Preferred substrates are derivativised forms of the known polysaccharide sepharose, particularly AH-Sepharose and CH-sepharose having respectively amino and carboxylate functional groups on their surface.

When AH- and CH-sepharoses are used to immobilise the corrin complex in this way, the reaction scheme for the immobilisation may be as below:

(where n is 0, 1 or 2). The amide, hydroxyl or carboxylic acid terminated substituent groups in the preferred complexes discussed above, eg $COR^1$, $COR^4$, $R^2$ and $R^3$ groups in 2J may in related ways be used to immobilise such complexes onto substrates, eg by interaction with functional groups of the substrate. For example $NH_2$ and COOH terminated $R^1$, $R^2$, $R^3$ and $R^4$ may form amide links, and COOH and OH terminated $R^2$, $R^3$ and $R^4$ may form ester links with appropriate functional sites on the substrate on immobilisation.

The complex may be bound directly to the substrate by standard methods, eg the use of a carbodiimide coupling agent. It is preferred to bind the corrin complex first to the substrate and then to add the metal ion. Binding of the corrin complex to the substrate may also use standard methods, eg the use of a carbodiimide, but a preferred method for binding the preferred complexes, eg those of formula 2J to a substrate which consists of a derivativised polysaccharide such as AH- or CH-Sepharose is to prepare a suspension of the substrate in a solution containing the appropriate corrin at pH7 then rapidly adjusting the pH to 12 followed by a rapid adjustment of the pH to 2, then finally rapidly adjusting the pH back to 7. The substrate plus immobilised corrin may then be filtered off, washed, and then exposed to a solution containing metal ions, to form the immobilised complex.

When the immobilised complex is prepared in this way it is preferred to use a ratio of the corrin complex to the substrate in which the amount of the corrin complex is in excess of that required to occupy all the available binding sites on the substrate so as to reduce any subsequent problem caused by the organic nitrogen compound binding to the substrate. It is also preferred to use an excess of the metal ion to ensure that as far as possible all the corrin rings contain a complexed metal ion.

According to a further aspect of the invention there is provided a water-insoluble substrate, having immobilised thereupon a corrin complex as defined above for use in the method described above for degradation of an organic nitrogen compound.

Suitable and preferred forms of such a substrate and immobilised complex are as indicated above. Such materials may be supplied separately for use in the method of the invention as discussed above, or for example contained in a cartridge through which an effluent solution to be degraded may be passed.

As mentioned above the method of the invention is preferably carried out with the organic nitrogen compound to be degraded dissolved in an aqueous solution. However the method may readily be applied to the degradation of organic nitrogen compounds dispersed or suspended in an aqueous medium or contained in a solid or a gas such as contaminated air.

For example to treat solids the solid may be dissolved or suspended in an aqueous medium so that the nitrogen compound partitions into the aqueous phase, where it is degraded. To treat gases, the gas may simply be bubbled through an aqueous medium containing the corrin complex and the reducing agent. In a preferred way of treating gases, the gas is passed through a column packed with a bed of a substrate having immobilised thereupon a metal-centred corrin complex as described above, and a current of an aqeous medium containing a dissolved reducing agent is also passed through the bed.

The invention also provides an apparatus for degradation of an organic nitrogen compound using the method of the invention. Preferably the apparatus uses a substrate having immobilised thereupon a complex immobilised thereupon as described above, and incorporates a bed of such a complex contained within a body and being capable of having a liquid or gas containing the compound passed through.

Advantageously in such an apparatus the body may be in the form of a replaceable cartridge containing the bed.

In a further way of carrying out the degradation method of the invention, a complex of the corrin either in a free form or immobilised on an immobilised substrate may be mixed with a suitable quantity of a reducing agent prior to use. Such a mixture may subsequently be introduced into an environment containing an organic nitrogen compound to be degraded, for example into used containers for these compounds prior to disposal.

BRIEF DESCRIPTION OF THE DRAWINGS

The invention will now be illustrated by way of example only with reference to FIG. 1 which shows the structures of the herbicides Dinoseb and Trifluralin, and the insecticide Parathion, and FIGS. 2 and 3 which show apparatus for degradation of effluent using the method of the invention.

(1) Hydrolysis of Cobalamin

Cobalamin (2A) (80 mg) was dissolved in 3M NaOH (20 ml) and incubated at 80° C. for 72 hr prior to gel-filtration using Fractogel TSK-40 (column dimensions 2×50 cm) equilibrated in water. The cobalamin fraction was eluted using water pumped at a flow rate of 30 ml/hr. Analysis of the cobalamin fraction by mass-spectroscopy indicated the loss of both the ribazole moiety and the amino groups around the corrin ring, leading to formation of cobyrinic acid or an isomer thereof.

(2) Complexing of corrin with ligands

Samples (15 μg) of commercially obtained cyanocobalamin were dissolved in 100 mM Tris/HCl buffer (150 μl), pH 9.0, prior to incubation with equimolar solutions of a variety of ligands at 37° C. for 30 min in the dark. Samples (10 μl) of the corrin/ligand complex were removed and assayed for ability to degrade nitrogen compounds. The absorbance spectrum of each sample was determined between 250 and 700 nm in a recording spectrophotometer (Shimadzu Model UV 240, V. A. Howe Ltd, London).

(3) Removal of Cyanide Ligands from Cobinamide.

Cobinamide (2Bi, having two CN ligands complexed to its central cobalt III ion) (10 mg) was dissolved in water (10 ml) prior to addition of 0.1M HCl to pH 2.0. The absorbance spectrum of the sample before and after acidification was determined between 250 and 700 nm in a recording spectrophotometer. The acidified sample was freeze-dried overnight and subsequently redissolved in 100 mM Tris/HCl buffer (10 ml), pH 9.0, and the pH adjusted to 9.0 by the addition of 0.01M NaOH. The absorbance spectrum of the sample was then redetermined. Samples (10 μl) were diluted in 100 mM Tris/HCl buffer (90 μl), pH 9.0, and 10 μl of this diluted material was assayed for the ability to degrade organic nitrogen compounds.

(4) Immobilisation of cobalamin onto CH-Sepharose 4B

CH-Sepharose 4B (2 g) was swollen in 0.5M NaCl (20 ml), and washed with this solution (400 ml). The Sepharose was then washed in demineralised water adjusted to pH 4.5 (100 ml). Cobalamin (2A) (40 mg) was dissolved in water (40 ml) and added to the Sepharose. The pH of the slurry was adjusted to pH 5.0, prior to the addition of EDC to a final concentration of 100 mM. The slurry was stirred overnight at room temperature in the dark, prior to washing with distilled water. Problems were encountered in the immobilisation of cobalamin onto CH-Sepharose 4B, probably due to the presence of the carbonyl group of the amide.

(5) Immobilisation of alkali-modified cobalamin onto AH-Sepharose

AH-Sepharose 4B (2 g) was swollen in 0.5M NaCl (20 ml), and washed with this solution (400 ml). The Sepharose was then washed in demineralised water adjusted to pH4.5 (100 ml). Alkali-modified cobalamin prepared as in 1 above (40 mg) was dissolved in water (40 ml) and added to the Sepharose. The pH of the slurry was adjusted to pH 5.0, prior to the addition of EDC to a final concentration of 100 mM. The slurry was stirred overnight at room temperature in the dark, prior to washing with distilled water.

(6) Immobilisation of alkali-modified cobalamin onto QAE-Sephadex A50

QAE-Sephadex A-50 (5 g) was mixed with alkali-modified cobalamin prepared as in 1 above (4 mg/ml; 100 ml) for 20 minutes, and the slurry then poured into a column and washed with distilled water (250 ml) prior to use.

(7) Immobilisation of corrins onto Amberlite XAD-2

Amberlite XAD-2 (4 g) was added to a solution of cobalamin (2A) (80 mg) dissolved in 100 mM Tris/HCl, pH 7, (20 ml). The amberlite was then washed in the same buffer (200 ml). It was found that washing of the substrate plus corrin with water led to a slow leaching of the cobalamin from the Amberlite.

(8) Immobilisation of modified cobalamin onto polystyrene beads

Alkali-modified cobalamin prepared as in 2 above was immobilised onto two types of polystyrene beads, differentiated by their functional groups, either hydrazide or alkylamine moieties.

Hydrazide-derivatized polystyrene beads (6 mm diameter) (25) were placed in a solution of alkali-modified cobalamin (4 mg/ml in water; 10 ml), and the pH adjusted to 5.5 prior to the addition of EDC to a final concentration of 100 mM. After mixing overnight at room temperature in the dark on a bottle-roller, the beads were washed with distilled water prior to use.

Alkylamine-derivatized polystyrene beads (25) were placed in a solution of alkali-modified cobalamin (4 mg/ml in water:ethanol (1:1; v:v); 10 ml), and the pH adjusted to 8.0. After mixing for 2 hours at room temperature in the dark on a bottle roller, the beads were washed with distilled water prior to use.

(9) Degradation of Nitrogen Compounds.

An aqueous solution was prepared containing a Tris/HCl buffer (pH 9), 5 mM iithiothreitol, 2 mM of the organic nitrogen compound and 50 µg/L of the corrin complex. The corrin complexes used were cyanocobalamin (2A) and cobinamide (2Bi). The reaction vessel was flushed with nitrogen, then incubated at 37° C. for 30 minutes. The mixture was extracted with 2 ml hexane:diethyl ether (85:15, v:v) and 0.5 µl of this extract was analysed by electron capture GLC. The chromatograph was equipped with a 1.5 m×4 mm silanised glass column, packed with 3% SE30 on a 100/120 mesh Supelcoport with nitrogen (40 ml/min) as the carrier gas. The injector and detector were maintained at 250° C., whilst the column oven was maintained at 190° C.

In order to assess the kinetics of degradation the following reaction mixture was used: 10 ml Tris/HCl buffer, pH 9.0 containing 5 mM DTT and 10 mg/l of the nitrogen compound. The mixture was equilibrated at 37° C. prior to the addition of 100 µL of a solution of the complex (1 µg/10 µL). The reaction vessel was purged with nitrogen then sealed with a butyl rubber septum and incubated at 37° C. At 5 minute intervals, a hypodermic syringe was used to withdraw 0.5 ml samples, which were extracted with 1 ml hexane:diethyl ether (85:15 v:v), and 0.5 µl of this extract was analysed by GLC as described above.

Results

The nitrogen compounds listed below were treated with a corrin complex as described above. Conversion to the product listed was quantitative at 37° C. after 5–10 minutes, the product being identified using gas liquid chromatography:

| Nitrogen Compound | Product |
|---|---|
| Nitrobenzene | Aniline |
| Nitrosobenzene | Aniline |
| 1,2-dinitrobenzene | 1,2-Diaminobenzene |
| 1,4-dinitrobenzene | 1,4-Diaminobenzone |
| Chloro-nitrobenzene | Chloro-aminobenzene |
| Nitrotoluene | Aminotolune |
| Nitrobenzoate | Aminobenzoate |
| Dinoseb | The corresponding $NH_2$-containing compounds. |
| Trifluralin | The corresponding $NH_2$-containing compounds. |
| Parathion | The corresponding $NH_2$-containing compounds. |

(10) Conversion of Aromatic Nitro- compounds to the corresponding Amino Derivatives using Immobilised Corrins.

100 mg of Vitamin B12 was dissolved in 3M sodium hydroxide, and incubated at 70° C. for 18 hours. On cooloing this was diluted to 100 ml in distilled water and the solution was mixed with 7 g of QAE Sephadex A-25 (Trade Mark, Pharmacia Chemicals, Upsala, Sweden). The slurry was packed into a chromatography column (volume 75 ml) and equilibrated with 100 mM Tris/HCl buffer pH 8.5. The column was operated at room temperature (20°).

The column was then re-equilibrated with Tris/HCl buffer pH 8.5 containing 25 µg/ml of 2-nitrotoluene at a flow rate of 1 ml $min^{-1}$. After equilibration Tris/HCl buffer pH8.5 containing 25 µg $ml^{-1}$ of 2-nitrotoluene and dithiothreitol (5 mM) was passed through the column at flow rates of 0.75, 1.5 and 3 ml $min^{-1}$.

At a flow rate of 0.75 ml $min^{-1}$ retention time in the column was 69 min. At 1.5 and 3 ml $min^{-1}$ retention times were 55 min and 17 min respectively. This is based on the working volume of the column being 52 $cm^3$.

At the slowest flow rate (0.75 ml $min^{-1}$) no 2-nitrotoluene could be detected in the effluent, it having been converted totally to 2-aminotoluene. At the intermediate flow rate of 1.5 ml $min^{-1}$, 2-aminotoluene was again undetectable. However, it had not all been converted into 2-aminotoluene at this flow rate as approximately 70% of it was present as 2aminotoluene and 30% as an intermediate.

At the highest flow rate of 3 ml $min^{-1}$ 2-nitrotoluene in the effluent was present at a concentration of 12.5 µg $ml^{-1}$, ie approximately 50% of the initial influent concentration.

(11) Degration Apparatus.

Figure 2:
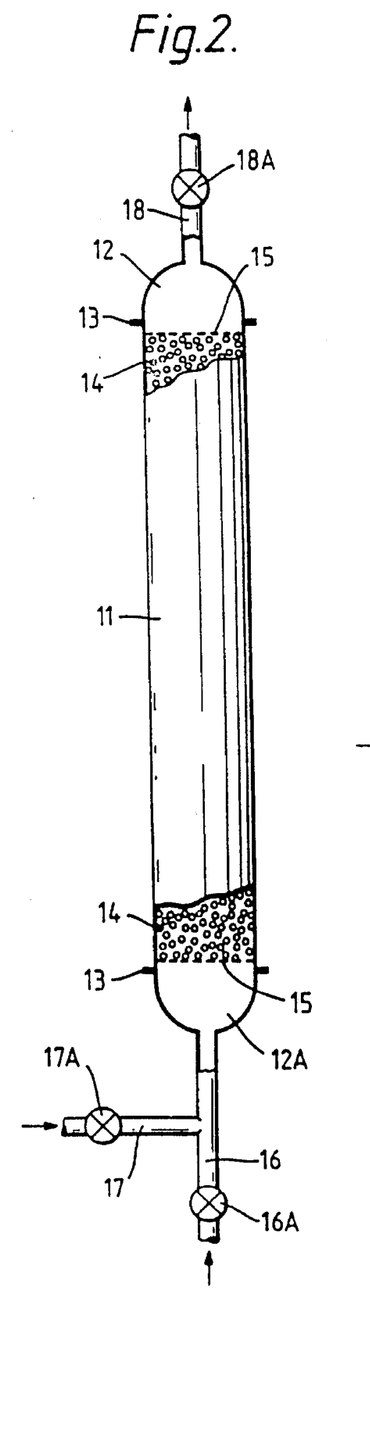
Figure 3:
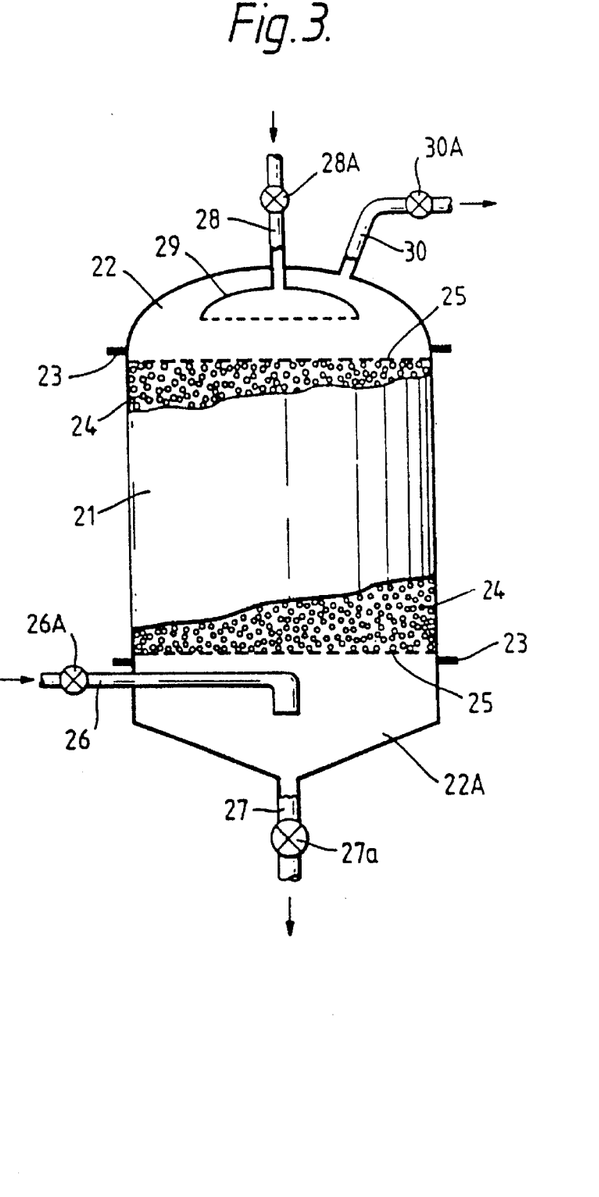

FIGS. 2 and 3 show respectively apparatus for the degradation of aqueous or gaseous effluent by the method of the invention.

The apparatus comprises a body (11, 21), having at its upper end an upper closure (12, 22) and at its lower end a lower closure (12A, 22A), the seals (13, 23) between the body (11, 21) and the closures (12, 12A, 22, 22A) being releasable but watertight or airtight as appropriate. Each body (11, 21) is largely filled with polystyrene beads (14, 24) having immobilised thereon a corrin complex eg 4–8 above retained in place in the body (11, 21) by retaining grids (15, 25).

In the lower closure (12A) are connected inlets (16), (17), through which flow may be controlled by valves (16A), (17A). The upper closure (12) is an outlet (18) flow through which may be controlled by a valve (18A).

In the lower closure (22A) is an inlet (26), and an outlet (27), and flow through these may be controlled by valves (26A) and (27A). In the upper closure (22) there is an inlet (28), flow through which may be controlled by valve (28A). The tube (28) communicates with a sprinkler (29) inside the closure (22). There is also an outlet (30) in the closure (20), flow through which is controlled by a valve (30A).

An aqueous effluent to be degraded is passed through inlet (16). A solution of a reducing agent is passed through inlet (17), mixing with the effluent. The mixture passes up the body (11) and contacts the beads (14), upon which degradation takes place. The degraded effluent leaves via outlet (18).

A gaseous effluent to be degraded is passed through inlet (26). At the same time a solution of a reducing agent is passed through inlet (28) so as to moisten all the beads (24) with the reducing solution. As the gaseous effluent contacts the beads (24), degradation of the effluent occurs, and the degraded effluent leaves via outlet (30). Excess reducing agent leaves via outlet (27) and may for example be treated with the apparatus of FIG. 1 or otherwise disposed of.

The grids (15, 25) prevent escape of the beads (14, 24). The effluent from outlets (18, 30) may be monitored, and when the beads (14, 24) appear to be exhausted, the seals (13, 23) may be released and a whole new body (11, 21) put in its place, ie as a replaceable degradation cartridge.

References

Mansuy D., Fontecave M. Biochemical and Biophsysical Research Communications (1982) 104(4) 1651–1657

Miwa G. T. Walsh J. S., Prog. Bas. Clin. Pharmac. (1988) 1 27–62

Lindeke B., Paulsen-Sörman U., Prog, Bas. Clin. Pharmac (1988) 1 63–102.

Stotter D. A., J-Inorg-Nuci Chem (1977), 39, 721–727.

Bieniek D., Mosa P. N., Klein W. and Korte F. (1970), Tetrahedron Lett. 47, 4055–4058.

Jagnow G., Haider K., Ellwart P. C., (1977), Arch-Microbiol, 115, 285.

Bonnet R., Godfrey J. M., Math V. B. J. Chem. Soc. (C) (1971) 3736–3743.

Gossauer A., Heise K. Götze H, Inhoffen H, Liebigs Ann. Chem. (1977) 1480–1499.

Borman D., Fischli A., Keese R., Eschenmoser A., Angew. Chem. Int. Edn. (1967) 6(10) 868–871 .

Bieganowski R., Friedrich W., Z. Naturforch. (1930) 36 9–15

Holze G. Gossauer A., Helv. Chim. Acta (1986) 69 1567–1570.

We claim:

1. A method of chemically reducing an organic nitrogen compound wherein the compound is reacted in an aqueous medium with a reducing agent in the presence of a complex of a corrin containing a metal-centered ring system of the formula:

in which $R^1$ is selected from $NH_2$ and OH; $R^2$ is selected from H, $CH_2CH_2COOH$ and $CH_2CH_2CONH_2$; $R^3$ is selected from H, $CH_2CH_2COOH$ and $CH_2CH_2CONH_2$; and $R^4$ is selected from $NHCH_2CH(OH)CH_3$, OH and $NH_2$ or the ring is that of cyanocobalamin; M is an ion or atom of a metal selected from group 2, 5, 6, 7, 8, 9, 10, 11 or 12 of the periodic table, A and B are the same or different co-ordinating ligands, and a and b are independently 0 or 1.

2. The method according to claim 1, wherein the nitrogen compound is an aliphatic or aromatic nitro- or nitroso-compound.

3. The method according to claim 2, wherein the nitrogen compound is an aromatic compound having one or more —$NO_2$,—NO or —$ONO_2$ groups attached directly to an aromatic ring.

4. The method according to claim 3, wherein the compound is selected from nitrobenzenes, dinitrobenzenes, nitrosobenzenes or analogues thereof having one or more alkyl, halogen or carboxylate substituents on the phenyl ring or on a side chain.

5. The method according to claim 4, wherein the nitrogen compound is selected from nitrobenzene, nitrosobenzene, dinitrobenzene, chloronitrobenzene, nitroalkylbenzene and nitrobenzoates.

6. The method according to claim 1, wherein the nitrogen compound is an aliphatic or aromatic thiocyanate, isothiocyanate or nitrile, N-oxide, oxime, azozy compound, nitroparaffin, nitro-olefin, halogenonitroparaffin, nitronitroso compound, nitrolic acid, nitroso-amine, nitroanine or nitroalkylhydrazine.

7. The method according to claim 3, wherein the nitrogen compound is selected from:

-continued

8. The method according to claim 1, wherein M is cobalt.

9. The method according to claim 8, wherein A and B are selected from $ClO^-4$, $SCN^-$, $SO^-_3$, $S_2O^-_3$, $H_2O$, $OH^-$, $CN^-$ and Cl.

10. The method according to claim 8, wherein the complex is a cobalt-centered complex as formed when cobalamin or neovitamin B12 is hydrolyzed by an aqueous alkali or acid.

11. The method according to claim 8, wherein the corrin complex is cobinamide, neocobinamide, cobyric acid, neocobryic acid, or an analogue thereof in which the $Co(CN)_2$ center is replaced by a CoAB center and where A and B are $Cl^-$ or $OH^-$.

12. The method according to claim 8, wherein the corrin complex is cobyrinic acid in which $R^1=R^4=OH$, $R^2=H$, $R^3=CH_2CH_2COOH$, or neocobyrinic acid in which $R^1=R^4=OH$, $R^2=CH_2CH_2COOH$, $R^3=H$, or an analogue thereof in which the $Co(CN)_2$ center is replaced by a CoAB center where A and B are $Cl^-$ or $OH^-$.

13. The method according to claim 1, wherein the corrin complex has been immobilized on an insoluble substrate and an aqueous solution containing the organic nitrogen compound is brought into contact with the immobilized complex.

14. The method according to claim 13, wherein the substrate is selected from derivatized polysaccharide, sepharose, cellulose, agarose, dextrose, dextran, polyacrylamide or copolymers thereof, derivatized inorganic oxide, glass beads, derivatized polystyrene or ion exchange resins, and the complex is immobilized thereon by chemical interaction between functional group substituents on the corrin ring and on the substrate.

15. A process for treating water or solids contaminated with at least one nitro- or nitroso-substituted compound comprising:

reducing said at least one nitro- or nitroso- substituted compound in an aqueous medium in the presence of an effective catalytic amount of at least one of a corrin- or porphyrin metal complex.

* * * * *